(12) United States Patent
Trevino et al.

(10) Patent No.: US 9,296,989 B2
(45) Date of Patent: *Mar. 29, 2016

(54) COMPOSITION AND METHOD FOR DELIVERY OF LIVING CELLS IN A DRY MODE HAVING A SURFACE LAYER

(75) Inventors: Ramiro Trevino, McKinney, TX (US); Steven R. Ellis, McKinney, TX (US)

(73) Assignee: DryLet LLC, McKinney, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 14/236,387

(22) PCT Filed: Apr. 3, 2012

(86) PCT No.: PCT/US2012/031997
§ 371 (c)(1),
(2), (4) Date: Jan. 31, 2014

(87) PCT Pub. No.: WO2012/138656
PCT Pub. Date: Oct. 11, 2012

(65) Prior Publication Data
US 2014/0206080 A1 Jul. 24, 2014

Related U.S. Application Data

(60) Provisional application No. 61/471,641, filed on Apr. 4, 2011.

(51) Int. Cl.
*C12N 5/071* (2010.01)
*C12N 5/00* (2006.01)
*A01N 1/02* (2006.01)

(52) U.S. Cl.
CPC ............ *C12N 5/0602* (2013.01); *A01N 1/0231* (2013.01); *C12N 5/0068* (2013.01); *C12N 2533/12* (2013.01)

(58) Field of Classification Search
CPC .................................................... C12N 5/0068
See application file for complete search history.

(56) References Cited

U.S. PATENT DOCUMENTS

| | | |
|---|---|---|
| 3,644,215 A | 2/1972 | Muller |
| 3,719,496 A | 3/1973 | Chen et al. |
| 3,726,693 A | 4/1973 | Harris et al. |
| 3,871,957 A | 3/1975 | Mohan et al. |
| 3,882,253 A | 5/1975 | Schafer et al. |
| 3,895,219 A | 7/1975 | Richardson et al. |
| 4,304,857 A | 12/1981 | Brouillard et al. |
| 4,426,570 A | 1/1984 | Hikino et al. |
| 4,486,651 A | 12/1984 | Atsumi et al. |
| 4,590,685 A | 5/1986 | Roth |
| 4,591,455 A | 5/1986 | Macedo et al. |
| 4,647,464 A | 3/1987 | Todd, Jr. et al. |
| 4,717,561 A | 1/1988 | Krivak et al. |
| 4,965,434 A | 10/1990 | Nomura et al. |
| 4,971,820 A | 11/1990 | Likuski et al. |
| 5,035,804 A | 7/1991 | Stowe |
| 5,077,461 A | 12/1991 | Hasegawa |
| 5,194,279 A | 3/1993 | Okel |
| 5,395,808 A | 3/1995 | Miller et al. |
| 5,403,799 A | 4/1995 | Miller et al. |
| 5,443,845 A | 8/1995 | Felix |
| 5,552,176 A | 9/1996 | Marino |
| 5,569,634 A | 10/1996 | Miller et al. |
| 5,635,214 A | 6/1997 | Ponchon et al. |
| 5,678,238 A | 10/1997 | Billings et al. |
| 5,906,843 A | 5/1999 | Dew et al. |
| 6,001,322 A | 12/1999 | Chevallier et al. |
| 6,184,408 B1 | 2/2001 | Burns et al. |
| 6,991,802 B1 | 1/2006 | Ahola et al. |
| 7,067,062 B2 | 6/2006 | Yang et al. |
| 7,153,521 B2 | 12/2006 | Viot |
| 7,422,737 B1 | 9/2008 | Nussinovitch et al. |
| 7,538,067 B2 | 5/2009 | Hu et al. |
| 2003/0026845 A1 | 2/2003 | Etzel et al. |
| 2003/0091641 A1 | 5/2003 | Tiller et al. |
| 2006/0019016 A1 | 1/2006 | Torcatis |
| 2006/0147546 A1 | 7/2006 | Ferlin et al. |
| 2007/0017195 A1 | 1/2007 | Witham et al. |
| 2007/0281063 A1 | 12/2007 | Carapelli |
| 2008/0071129 A1 | 3/2008 | Yang et al. |
| 2009/0114569 A1 | 5/2009 | Osaheni et al. |
| 2009/0120872 A1 | 5/2009 | Kroh |
| 2009/0211453 A1 | 8/2009 | Nassivera et al. |
| 2009/0214701 A1 | 8/2009 | Forchhammer et al. |
| 2009/0232950 A1 | 9/2009 | Brothers, Jr et al. |

FOREIGN PATENT DOCUMENTS

| | | |
|---|---|---|
| EP | 0 067 459 A1 | 12/1982 |
| EP | 1 048 697 A2 | 11/2000 |
| FR | 2 573 772 A1 | 5/1986 |

(Continued)

OTHER PUBLICATIONS

Teramura et al. "Islet-encapsulation in ultra-thin layer-by-layer membranes of poly(vinyl alcohol) anchored to poly(ethylene glycol)-lipids in the cell membrane", Biomaterials, 2007, 28:4818-4825.*
Baca et al. "Cell-directed assembly of bio-nano interfaces-a new scheme for cell immobilization", Acc. Chem. Res. 2007, 40:836-845.*
Feller et al. "Polyunsaturated fatty acids in lipid bilayers: intrinsic and environmental contributions to their unique physical properties", JACS, 2002, 124(2):318-326.*
Huang et al. "Highly efficient cellular labeling of mesoporous nanoparticles in human mesenchymal stem cells: implication for stem cell tracking", The FASEB J., 2005, 19:2014-2016.*
Harper et al. ACSNANO, 2010, 4(10):5539-5550.*
PCT International Search Report and Written Opinion dated Jun. 25, 2012; International Application No. PCT/US2013/031997; International File Date.: Apr. 3, 2012.

(Continued)

*Primary Examiner* — Bin Shen
(74) *Attorney, Agent, or Firm* — Dentons US LLP

(57) ABSTRACT

The present invention generally relates to compositions and methods of delivering living cells in a dry mode, wherein the compositions include a surface layer disposed on the outer surface of the composition that is permeable to carbon dioxide and oxygen. The compositions may be used to deliver living cells to a delivery point without the use of expensive refrigerants such as dry ice or liquid nitrogen.

24 Claims, 1 Drawing Sheet

(56) References Cited

FOREIGN PATENT DOCUMENTS

| | | | |
|---|---:|---|---|
| GB | 736919 | A | 9/1955 |
| GB | 886533 | | 1/1962 |
| GB | 938381 | | 10/1963 |
| GB | 1253271 | | 11/1971 |
| GB | 1262838 | | 2/1972 |
| WO | 8303102 | | 9/1983 |
| WO | 8303102 | A1 | 9/1983 |
| WO | 9812491 | A1 | 3/1998 |
| WO | 2007139264 | A1 | 6/2007 |
| WO | 2008061363 | A1 | 5/2008 |
| WO | 2008121078 | A1 | 10/2008 |
| WO | 2010094747 | A1 | 8/2010 |
| WO | 2010/108211 | A1 | 9/2010 |

OTHER PUBLICATIONS

PCT International Search Report and Written Opinion dated Sep. 1, 1998; International Application No. PCT/US1998/012491; International File Date.: Mar. 20, 1998.

Liu, J., et al.; Porous Nanoperticle Supported Lipid Bilayers ((Protocells) as Delivery Vehicles; Journal of the American Chemical Society; Feb. 4, 2009; pp. 1354-1355; vol. 131, No. 4; 2009 American Chemical Society.

Wang, L-S., et al.; Biofunctionalized Phospholipid-Capped Mesoporous Silica Nanoshuttles for Targeted Drug Delivery; Improved Water Suspensibility and Decreased Nanospecifio Protein Binding; ACS Nano; Aug. 24, 2010; pp. 4371-4379; vol. 4, No. 8; 2010 ACS NANO.

\* cited by examiner

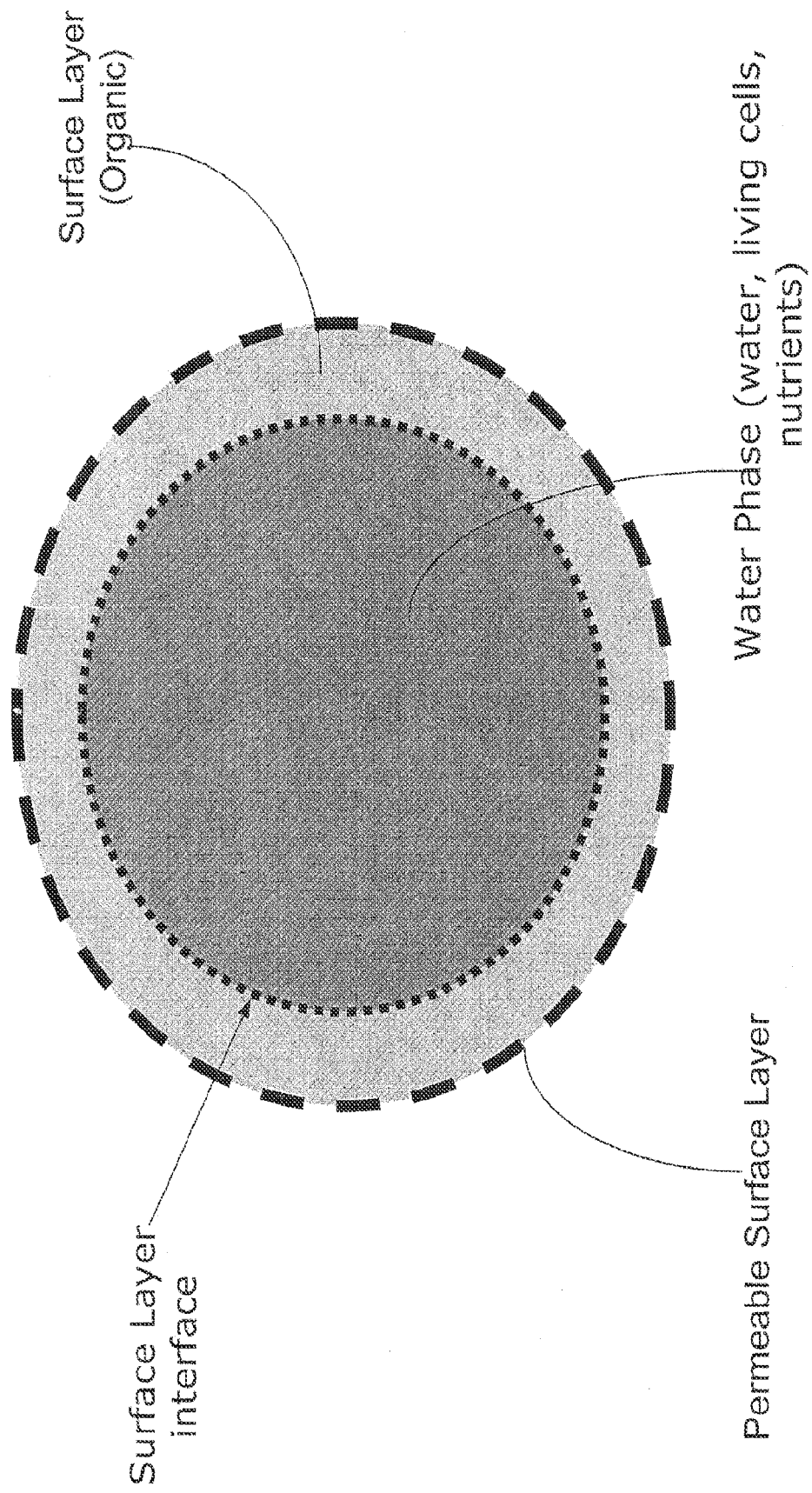

COMPOSITION AND METHOD FOR DELIVERY OF LIVING CELLS IN A DRY MODE HAVING A SURFACE LAYER

This application is the national stage application of International Application No. PCT/US2012/031997, filed Apr. 3, 2012, which claims the benefit of U.S. Provisional Application No. 61/471,641, filed Apr. 4, 2011.

BACKGROUND OF THE INVENTION

1. Field of the Invention

The present invention generally relates to compositions and methods of delivering living cells in a dry mode. More specifically, the present invention relates to compositions and methods of delivering living cells in a dry mode having a surface layer.

2. Description of the Related Art

It is very difficult to deliver various substances in a dry form. For example, living cells are typically not sustainable in a dry, non-frozen state. Normally, these living cells are freeze dried and then transported with liquid nitrogen to keep them frozen during transport; however, this leads to increased costs and difficulties for transporting and handling of the frozen living cells. Therefore, it would be advantageous to provide compositions and methods for delivery of living cells in a dry form that did not require the use of refrigerants such as liquid nitrogen.

SUMMARY OF THE INVENTION

The present invention is directed to compositions and methods that satisfy at least one of these needs. The present invention relates to compositions having a surface layer and methods of delivering living cells as part of a composition in a dry mode. Exemplary living cells can include human cells, primary cells, cell lines, immortalized cells, lymphatic cells, cell tissue, serum, and combinations thereof.

One embodiment of the invention is a composition for delivering living cells in a dry mode that contains an inert carrier substrate having a porous structure, living cells loaded throughout the pores of the inert carrier substrate, and a surface layer disposed on the outer surface of the inert carrier substrate. In one embodiment, the surface layer can be permeable, such that the surface layer allows for movement of certain particles that aid in sustaining and/or propagating new cell growth of the living cells loaded throughout the inert carrier substrate. In one embodiment, the surface layer can be permeable to oxygen and carbon dioxide such that the composition is operable to allow for increased propagation of the living cells within the pores of the inert carrier substrate as compared to another composition having an absence of the surface layer. As used herein, propagation refers to the ability of a substance to reproduce. In one embodiment, the surface layer is operable to allow for oxygen exchange, nutrient exchange, respiration, carbon dioxide production and digestion, and enzyme production.

In one embodiment, the inert carrier substrate is selected from the group consisting of diatomaceous earth, walnut and pecan shells, rice hulls, cellulosic clay, montmorillonite clay, bentonite clay, wool, cotton, cellulose, corn cobs, cellulose shells, precipitated silica, and combinations thereof. In one embodiment, the inert carrier substrate can be precipitated silica.

In one embodiment, the surface layer can include an organic phase. Organic phase as used herein with respect to the surface layer means a phase that includes any member of a large class of chemical compounds whose molecules contain carbon. In one embodiment, the organic phase can be lipids, polysaccharides, fatty acids, or combinations thereof. In one embodiment, the fatty acids have between 12 and 20 carbon atoms. In one embodiment, the organic phase can include nonionic plant-based surfactants. Preferable pant-based surfactants include, without limitation, polysorbate 20 and polysorbate 80. Additional exemplary surfactants, without limitation, can also include cocamidopropyl betaine, sodium lauroyl lactylate, capylol, capric glucoside, and combinations thereof. In one embodiment, non-ionic surfactants are preferred.

In one embodiment, the organic phase can include fatty acid alcohols, fatty acids, lipids and lethicin. In one embodiment, the fatty acid alcohols have between 12 and 20 carbon atoms. In one embodiment, the fatty acid alcohols can include cetearyl alcohol and cetyl ester. In one embodiment, the fatty acid can be saturated, unsaturated, or a combination thereof. Exemplary saturated fatty acids, without limitation, include: palmitic acid, steric acid, arachidic acid, behenic acid, myristic acid, lignoceric acid, and combinations thereof. Exemplary unsaturated fatty acids, without limitation, include: oleic acid, palmitoleic acid, linoleic acid, linolenic acid, Omega-3, Omega-6, and combinations thereof. In one embodiment, possible sources of the fatty acids can include coconut oils, palm oils, vegetable oils, fish oils, and combinations thereof.

In one embodiment, the organic phase can be formed when an emulsion is mixed with the inert carrier substrate. Furthermore, the emulsion can be formed by mixing a combination of ingredients, wherein the ingredients are selected from the group consisting of lipids, polysaccharides, fatty acids, lethicin, plant-based surfactants, emulsifiers, and combinations thereof.

In another embodiment, the surface layer is substantially impermeable to water. In another embodiment, the surface layer is substantially impermeable to deionized water. In one embodiment, the surface layer can be broken down by surfactants, oil, organic solvents, salt water, damp soil, or combinations thereof. In another embodiment, the surface layer is at least partially soluble to surfactants, oil, organic solvents, salt water, damp soil, or combinations thereof. In another embodiment, the surface layer can further include an absence of a protein.

In another embodiment, the surface layer can include squalene, squalane, C40 isoprenoids, phosphatidylglycerol, diphosphatidylglycerol, cardiolipin, phosphatidylethanolamine, monoglycerol phosphate, or combinations thereof.

In another embodiment, the composition for delivering living cells in a dry mode can be practiced without zeolites, aluminosilicates, mineral powder, and/or an acidic polymer. In one embodiment, the composition is operable to breakdown hydrocarbon deposits in water or soil when applied in a dry state. In another embodiment, the composition can also include nutrients loaded in the inert carrier substrate, such that the nutrients are in contact with the living cells, wherein the nutrients are operable to provide a food source to the living cells loaded throughout the pores of the inert carrier substrate to enhance propagation of the living cells. Non-limiting examples of nutrients include glucose, inulin, and combinations thereof.

In another embodiment, the pores of the precipitated silica define a distribution of pore sizes, where a substantial amount of pores have diameters within the range of 38 to 240 nanometers. In another embodiment, the nutrients can be ammonia, nitrogen, ammonium nitrogen, urea, dextrose, dextrin, sugars, or combinations thereof. In another embodiment, the composition has an initial living cell count, and the composition is operable to maintain approximately 50 to 400% of the initial microorganism count for a period of time, preferably at least 45 days.

As used herein, the term "fluid" is to be understood to include liquids, plasmas, and gases.

In another embodiment, a composition for delivering a living cell in a dry mode that maintains flow contains an inert carrier substrate having a porous structure, a surface layer disposed on the outer surface of the inert carrier substrate, wherein the surface layer is permeable to oxygen and carbon dioxide, and the living cell is loaded throughout the pores of the inert carrier substrate, the composition having 25 to 75% living cell concentration by weight, the composition operable to maintain approximately 75 to 100% of the living cell concentration for a period of time, preferably at least 45 days, wherein the composition is soluble in water and the composition maintains its ability to readily flow. In another embodiment, the composition can have more than one type of living cell.

In another embodiment, the composition contains an inert carrier substrate having silica pores, a surface layer disposed on the outer surface of the inert carrier substrate, wherein the surface layer is permeable to oxygen and carbon dioxide, and a living cell loaded into the inert carrier substrate, wherein the average pore diameter of the living cell's molecules is less than the average diameter of the silica pores, and wherein the composition is operable to transport the living cells in a dry mode without significant degradation or the use of externally supplied refrigerants.

In another embodiment, the composition is formed without the use of a reaction. In another embodiment, the composition is formed without chemically altering the surface of the inert carrier substrate. In another embodiment, the composition is substantially dry such that it can readily flow. In one embodiment, the composition can exhibit an angle of repose between 29.9° and 42°. In one embodiment, the angle of repose can be determined by pouring the composition through a funnel and allowing the composition to fall onto a base board, thereby forming a conical mound. A portion of the base board can then be removed from underneath a portion of the conical mound. The angle formed by the edge of the board can be measured using a straight edge and reading the angle. In another embodiment, the composition has a Carr index value below 15. The Carr index is an indication of the compressibility of a powder. It is calculated by the formula:

$$C = 100\frac{V_T - V_B}{V_T},$$

where $V_B$ is the freely settled volume of a given mass of powder, and $V_T$ is the tapped volume of the same mass of powder. The Can index can also be expressed as:

$$C = 100 \times \left(1 - \frac{\rho_B}{\rho_t}\right),$$

where $\rho_B$ is the freely settled bulk density of the powder, and $\rho_T$ is the tapped bulk density of the powder. In another embodiment, the composition is not hygroscopic.

In another embodiment, an additional benefit is that the composition has an increased shelf life and/or can provide additional stability not accomplishable in a fluid state. For example, living cells that are kept at atmospheric pressure and at room temperature often times degrade after a few weeks, which means the end user must use the fluid substances quickly. In certain embodiments, these relatively unstable living cells can be loaded into precipitated silica to increase their shelf life and/or provide additional stability not accomplishable in a fluid state. As used herein, shelf life generally means the recommendation of time that products can be stored, during which the defined quality of a specified proportion of the goods remains acceptable under expected (or specified) conditions of distribution, storage and display. Some substances in their fluid states are relatively unstable.

In another embodiment, living cells and nutrients can be delivered in a dry format. Exemplary nutrients include, without limitation, glucose, inulin, and combinations thereof. In another embodiment, the delivery of these living cells and nutrients can be achieved by loading precipitated silica with the living cells, the nutrients, and an organic phase, together or separately, to a desired capacity such that a surface layer forms on the outer surface of the inert carrier substrate, while the living cells and the nutrients remain loaded throughout the pores of the inert carrier substrate. The composition can then be used to transport the living cells in a substantially free flowing, dry mode without the need for any type of external refrigeration.

In another embodiment, a method for increasing the viability of living cells can include loading an inert carrier substrate with an emulsion to a desired capacity to form a loaded product. In one embodiment, the emulsion can include an organic phase and a water phase, wherein the water phase can include water and living cells. In another embodiment, the water phase can further include nutrients, wherein the nutrients are water soluble. In another embodiment, the organic phase can include nonionic surfactants. Nonionic plant-based surfactants are also acceptable. In another embodiment, the organic phase can include fatty acid alcohols, fatty acids, lipids, and lethicin. In another embodiment, the organic phase can include lipids, fatty acids, and polysaccharides.

Embodiments of the present invention provide many benefits over conventional storage and handling of living cells, including ease of use, lower shipping cost, ease of transportation, reduced storage requirements, and elimination of externally provided refrigerants.

BRIEF DESCRIPTION OF THE DRAWINGS

These and other features, aspects, and advantages of the present invention will become better understood with regard to the following description, claims, and accompanying drawings. It is to be noted, however, that the drawings illustrate only several embodiments of the invention and are therefore not to be considered limiting of the invention's scope as it can admit to other equally effective embodiments.

FIG. 1 is a cross sectional diagram of a composition in accordance with an embodiment of the present invention.

DETAILED DESCRIPTION OF EMBODIMENTS OF THE PRESENT INVENTION

Embodiments of the present invention allow for the delivery of substances in a dry mode. In its most basic format, a predetermined amount of substance, if initially in liquid format, is added to an amount of an inert carrier substrate and mixed to form a loaded product having a semi-permeable surface layer. If the substance is initially in a dry format, the substance can be liquefied by various means known in the art and then added to an amount of the inert carrier substrate and mixed to form a loaded product. The loaded product has the consistency of a dry, sand-like substance. The loaded product includes the inert carrier substrate and the liquid additive loaded throughout the inert carrier substrate inner and outer surfaces, and a surface layer on the outer surface of the inert carrier substrate. In one embodiment, the surface layer is permeable to carbon dioxide and oxygen. Additionally, the surface layer includes an organic phase that can be made using a variety of techniques. The loaded product contains the characteristics of the substance, yet is dry to the touch. In one embodiment, the surface layer does not rub off or leave an oily feel to the skin.

In one embodiment of the invention, a composition for delivering living cells in a dry mode contains the inert carrier substrate having a porous structure, a surface layer permeable to carbon dioxide and oxygen, and living cells loaded throughout the pores of the inert carrier substrate. In another embodiment, the pores of the inert carrier substrate have diameters within the range of 38 to 240 nanometers. In another embodiment, the living cells are selected from the group of human cells, primary cells, cell lines, immortalized cells, lymphatic cells, cell tissue, serum, and combinations thereof. In another embodiment, the composition can also include nutrients loaded throughout the pores of the inert carrier substrate. In another embodiment, the nutrients are selected from the group consisting of ammonia, nitrogen, ammonium nitrogen, urea, dextrose, dextrin, sugars, inulin, and combinations thereof. In another embodiment, the composition has an initial living cell count, and the composition is operable to maintain approximately 75 to 400% of the initial living cell count for a period of time, preferably at least 45 days. In one embodiment, the surface layer acts similarly to cell walls that can be found in bacteria (prokaryotes) and fungi (eukarotes), thereby supporting cellular life and propagation.

As noted previously, precipitated silica can be used in some embodiments of the present invention as the inert carrier substrate. The characteristics of typical precipitated silica are as follows: pore size range from 38-240 nanometers and a particle size of 10-1400 microns. Examples of precipitated silica useful as part of certain embodiments of compositions and methods of the present invention are the FLO-GARD® or HI-SIL® silicon dioxide products obtained from PPG Industries, Inc. Precipitated silica may also be obtained from other providers, such as for example, W.R. Grace and Company. Another characteristic of typical precipitated silica is a surface area of from about 140 to about 160 square meters per gram.

Examples of living cells to be used in certain embodiments of the present invention include human cells, primary cells, cell lines, immortalized cells, lymphatic cells, cell tissue, serum, and combinations thereof.

Preferred Method for Making the Loaded Product Containing Living Cells

What follows is an example of how one can load living cells into precipitated silica granules. Add an appropriate amount of fatty acid and emulsifier into a stainless steel mixing container. Optionally, heat the resulting mixture to 60° C. for approximately five minutes. The mixture is mixed at a moderate speed until the mixture is sufficiently emulsified. If heated, allow the mixture to cool down to room temperature while continuing to mix. The mixture is preferably mixed sufficiently enough to form a homogenized mixture. In a separate container, the primary cells are processed in a commercial food processor and then preferably stored at 3° C. An appropriate amount of nutrients are added to water at room temperature. 50 grams of primary cells (bovine liver in this case) are then added and mixed at room temperature. This mixture of nutrients, water, and primary cells is then added to the container with the homogenized mixture and then mixed well to form a liquid media. The liquid media is then added to an appropriate amount of FLO-GARD SC72C precipitated silica granules while mixing using a stainless steel ribbon blender until all the liquid media is substantially loaded into the precipitated silica granules. Generally speaking, approximately 2 parts liquid media is added to 1 part precipitated silica granules. The resulting product is dry to the touch within five minutes of the initial introduction of the liquid media. This dry state is reached during the stirring of the combined ingredients and is handled as a dry product immediately upon unloading the mixer. The loaded product can be then stored at room temperature with an improved shelf life; however, it is preferably stored in a refrigerator at a temperature of approximately 33° F.-80° F., more preferably 35° F. to 50° F., and more preferably about 38° F. While this embodiment combined the solutions in this manner, it should be understood that they may be combined in other orders.

In order to release the living cells from the precipitated silica, the user need only combine the loaded product with water or saline solution in an amount exceeding the precipitated silica's saturation point. The surface layer of the loaded product is broken down during this step, which allows the living cells to be released. The living cells can then be isolated from this solution using known techniques in the art, for example, centrifugation.

As used herein, the term "dry mode" means that a liquid is substantially loaded in the inert carrier substrate. One of ordinary skill in the art will understand that this is achieved during the mixing process when a liquid is loaded into the inert carrier substrate. In one embodiment, after mixing for five minutes, the resulting product is dry to the touch and can be handled as a dry product. Furthermore, the dry product is fully free flowing.

Various compositions of the liquid media were created varying the type of fatty acids, the type of nutrients, and the types of emulsifiers. A summary can be found in Table I below:

TABLE I

Preparation of the Liquid Media

| | Fatty Acid | | Emulsifier | | | | Nutrient | | Distilled | Total |
|---|---|---|---|---|---|---|---|---|---|---|
| Sample | Lethicin | Olive Oil | Cocamidopropyl Betaine & Sodium Lauroyl lactylate | Capylol/ Capric glucoside | Polysorbate 20 | Polysorbate 80 | glucose | Inulin | Water | Weight |
| 1 | 200 | — | 200 | — | — | — | 50 | — | 900 | 1350 |
| 2 | 200 | — | — | 200 | — | — | 50 | — | 900 | 1350 |
| 3 | 200 | — | — | — | 200 | — | 50 | — | 900 | 1350 |
| 4 | 200 | — | — | — | — | 300 | 50 | — | 880 | 1430 |
| 5 | 200 | — | 200 | — | — | — | — | 50 | 900 | 1350 |

TABLE I-continued

Preparation of the Liquid Media

| | Fatty Acid | | Emulsifier | | | | Nutrient | | Distilled | Total |
|---|---|---|---|---|---|---|---|---|---|---|
| Sample | Lethicin | Olive Oil | Cocamidopropyl Betaine & Sodium Lauroyl lactylate | Capylol/ Capric glucoside | Polysorbate 20 | Polysorbate 80 | glucose | Inulin | Water | Weight |
| 6  | 200 | —   | —   | 200 | —   | —   | —  | 50 | 900 | 1350 |
| 7  | 200 | —   | —   | —   | 200 | —   | —  | 50 | 900 | 1350 |
| 8  | 100 | 100 | —   | —   | —   | 300 | —  | 50 | 880 | 1430 |
| 9  | 100 | 100 | 200 | —   | —   | —   | 50 | —  | 900 | 1350 |
| 10 | 100 | 100 | —   | 200 | —   | —   | 50 | —  | 900 | 1350 |
| 11 | 100 | 100 | —   | —   | 200 | —   | 50 | —  | 900 | 1350 |
| 12 | 100 | 100 | —   | —   | —   | 300 | 50 | —  | 880 | 1430 |
| 13 | 100 | 100 | 200 | —   | —   | —   | —  | 50 | 900 | 1350 |
| 14 | 100 | 100 | —   | 200 | —   | —   | —  | 50 | 900 | 1350 |
| 15 | 100 | 100 | —   | —   | 200 | —   | —  | 50 | 900 | 1350 |
| 16 | 100 | 100 | —   | —   | —   | 300 | —  | 50 | 880 | 1430 |

In another embodiment, a composition for delivering a liquid media in a dry mode contains the inert carrier substrate having silica pores, a surface layer disposed on the outer surface of the inert carrier substrate, wherein the surface layer is permeable to oxygen and carbon dioxide, and a liquid media loaded into the inert carrier substrate, wherein the average pore diameter of the liquid media's molecules is less than the average diameter of the silica pores. In another embodiment, the liquid media includes an emulsifier, a dilutant, nutrients, amino acids, fatty acids, and living cells. In another embodiment, the composition is formed without the use of a reaction. In another embodiment, the composition is formed without chemically altering the surface of the inert carrier substrate. In another embodiment, the composition is substantially dry such that it can readily flow. In another embodiment, the composition is not hygroscopic.

In another embodiment, the invention relates to the use of the inert carrier substrate as a delivery agent for the substance in a dry mode. In an embodiment, if the substance is in solid form, then it can be liquefied by mixing the substance in a carrier fluid, such as water, alcohol, glycerin, syrup, oil, acetone or other acceptable fluid media. Once the substance is in a liquid state, it can be directly added and mixed with inert carrier substrate such that the substance infuses throughout the inert carrier substrate to form a loaded product.

In another embodiment, the composition can be created by combining a wax, cetearyl alcohol, a fatty acid, an emulsifier, water, and living cells. In one embodiment, the wax can include bees wax. In another embodiment, the fatty acids can include olive oil, canola oil, sunflower oil, vegetable oil, or combinations thereof. In another embodiment, the emulsifier can be lethicin. In one embodiment, the wax can be present in an amount from 1% to 40%, more preferably 10% by weight. In one embodiment, the cetearyl alcohol can be present in an amount from 1% to 15%, more preferably 2% by weight. In one embodiment, the fatty acids can be present in an amount from 2% to 40%, more preferably 15% by weight. In one embodiment, the emulsifier can be present in an amount from 1% to 7%, more preferably 3% by weight. In one embodiment, the water/primary cell solution can be present in an amount from 1% to 50%, more preferably 2-3% by weight. In one embodiment, the water/primary cell solution contains 70% to 99% water, more preferably 97% water, and 1% to 30% living cells, more preferably 3% living cells by volume.

In another embodiment, the composition can be created by combining a wax, cetearyl alcohol and/or cetyl ester, a fatty acid, an emulsifier, water, and living cells. In one embodiment, the wax can include bees wax. In another embodiment, the fatty acids can include olive oil, canola oil, sunflower oil, vegetable oil, or combinations thereof. In another embodiment, the emulsifier can be lethicin. In one embodiment, the wax can be present in an amount from 1% to 40%, more preferably 10% by weight. In one embodiment, the cetearyl alcohol can be present in an amount from 1% to 15%, more preferably 2% by weight. In one embodiment, the cetyl ester can be present in an amount from 1% to 15%, more preferably 2% by weight. In one embodiment, the fatty acids can be present in an amount from 2% to 40% more preferably 15% by weight. In one embodiment, the emulsifier can be present in an amount from 1% to 7%, more preferably 3% by weight. In one embodiment, the water/primary cell solution can be present in an amount from 1% to 50%, more preferably 2-3% by weight. In one embodiment, the water/primary cell solution contains 70% to 99% water, more preferably 97% water, and 1% to 30% living cells, more preferably 3% living cells by volume.

In one embodiment, the water/microorganism solution can contain 98% water and 2% living cells by volume. In another embodiment, the water/microorganism solution can contain between 95% to 98% water and 2% to 5% living cells as measured by volume.

FIG. 1 represents a cross sectional view of a loaded product having a surface layer that is loaded with water, living cells, emulsifiers, and nutrients. As shown in FIG. 1, the water phase is located within the pores of the inert carrier substrate. A surface layer interface can be formed between the surface layer and the water phase. The dashed lines of the surface layer interface and the surface layer are representative of the advantageous permeability of the surface layer, which allows for oxygen and carbon dioxide to move in and out of the loaded product. This keeps the water phase within the loaded product while also allowing for the living cells to "breathe," which aids in propagation. Additionally, the surface layer keeps the replication controlled and contained within the surface layer interface.

Those skilled in the art will recognize that many changes and modifications can be made to the method of practicing the invention without departing the scope and spirit of the invention. In the drawings and specification, there have been disclosed embodiments of the invention and, although specific terms are employed, they are used in a generic and descriptive sense only and not for the purpose of limitation, the scope of the invention being set forth in the following claims. The invention has been described in considerable detail with specific reference to these illustrated embodiments. It will be apparent, however, that various modifications and changes can be made within the spirit and scope of the invention as described in the foregoing specification. Furthermore, language referring to order, such as first and second, should be understood in an exemplary sense and not in a limiting sense. For example, it can be recognized by those skilled in the art that certain steps can be combined into a single step.

U.S. Provisional Application 61/390,029, filed on Oct. 5, 2010 is herein incorporated by reference in its entirety.

Having described the invention above, various modifications of the techniques, procedures, materials, and equipment will be apparent to those skilled in the art. While various embodiments have been shown and described, various modifications and substitutions may be made thereto. Accordingly, it is to be understood that the present invention has been described by way of illustration(s) and not limitation. It is intended that all such variations within the scope and spirit of the invention be included within the scope of the appended claims. The singular forms "a", "an" and "the" may include plural referents, unless the context clearly dictates otherwise. Moreover, the present invention may suitably comprise, consist or consist essentially of the elements disclosed and may be practiced in the absence of an element not disclosed.

What is claimed is:

1. A composition for delivering living cells in a dry mode, the composition comprising:

an inert carrier substrate having pores;

living cells loaded within the pores of the inert carrier substrate; and a surface layer disposed on an outer surface of the inert carrier substrate loaded with the living cells, wherein the surface layer is permeable to molecules that aid in cell growth of the living cells such that the composition is operable to allow for increased propagation of the living cells within the inert carrier substrate as compared to another composition having an absence of the surface layer.

2. The composition as claimed in claim 1, wherein the molecules that permeate the surface layer include oxygen and carbon dioxide.

3. The composition as claimed in claim 1, wherein the inert carrier substrate is selected from the group consisting of diatomaceous earth, walnut and pecan shells, rice hulls, cellulosic clay, montmorillonite clay, bentonite clay, wool, cotton, cellulose, corn cobs, cellulose shells, precipitated silica, and combinations thereof.

4. The composition as claimed in claim 1, wherein the inert carrier substrate is precipitated silica.

5. The composition as claimed in claim 1, wherein the surface layer comprises an organic phase.

6. The composition as claimed in claim 5, wherein the organic phase comprises a fatty acid.

7. The composition as claimed in claim 6, wherein the fatty acid is an unsaturated fatty acid.

8. The composition as claimed in claim 1, wherein the surface layer is substantially impermeable to water.

9. The composition as claimed in claim 1, wherein the surface layer is substantially insoluble to deionized water.

10. The composition as claimed in claim 1, wherein the surface layer is susceptible to surfactants, oil, organic solvents, salt water, damp soil, or combinations thereof.

11. The composition as claimed in claim 1, wherein the surface layer is at least partially soluble to surfactants, oil, organic solvents, salt water, damp soil, or combinations thereof.

12. The composition as claimed in claim 1, wherein the surface layer further comprises an absence of a protein.

13. The composition as claimed in claim 1, further comprising an absence of zeolites.

14. The composition as claimed in claim 1, further comprising an absence of aluminosilicates.

15. The composition as claimed in claim 1, further comprising an absence of a mineral powder.

16. The composition as claimed in claim 1, wherein the living cells are selected from the group consisting of human cells, primary cells, cell lines, immortalized cells, lymphatic cells, and combinations thereof.

17. The composition as claimed in claim 1, further comprising an absence of an acidic polymer.

18. The composition as claimed in claim 1, further comprising nutrients in contact with the living cells, wherein the nutrients are operable to provide a food source to the living cells loaded throughout the inert carrier substrate such that the living cells can propagate.

19. The composition as claimed in claim 18, wherein the nutrients are selected from the group consisting of ammonia, nitrogen, ammonium nitrogen, urea, dextrose, dextrin, sugars, and combinations thereof.

20. The composition as claimed in claim 1, wherein the inert carrier substrate has pores that have diameters within the range of 38 to 240 nanometers.

21. The composition as claimed in claim 1, wherein the composition has an initial living cell count, and the composition is operable to maintain approximately 50 to 400% of the initial living cell count for at least 45 days.

22. A composition for delivering living cells in a dry mode, the composition comprising:

an inert carrier substrate having pores;

a surface layer disposed on an outer surface of the inert carrier substrate loaded with the living cells, wherein the surface layer is permeable to oxygen and carbon dioxide; and living cells loaded within the pores of the inert carrier substrate, the composition having 25 to 75% living cell by weight, the composition operable to maintain approximately 50 to 100% of the living cell by weight for a period of at least 45 days.

23. The composition as claimed in claim 22, wherein the composition is substantially dry.

24. The composition as claimed in claim 22, wherein the composition is not hygroscopic.

* * * * *